United States Patent [19]

Potter

[11] 4,305,389
[45] Dec. 15, 1981

[54] RACK FOR A FOOT-OPERATED ANESTHETIC GAS BAG

[76] Inventor: Glenn J. Potter, 1332 S. Hope St., Apartment 302, Los Angeles, Calif. 90015

[21] Appl. No.: 174,722

[22] Filed: Sep. 15, 1980

[51] Int. Cl.³ .......................................... A61M 16/00
[52] U.S. Cl. ......................... 128/205.13; 128/205.17; 92/161; 248/95; 248/99; 417/235
[58] Field of Search ...................... 128/205.13, 205.14, 128/205.15, 205.16, 205.17, 203.28, 203.13; 92/91, 92, 161; 248/95, 99; 417/234, 235

[56] References Cited

U.S. PATENT DOCUMENTS

| | | | |
|---|---|---|---|
| 224,370 | 2/1880 | Wilson | 92/92 |
| 527,248 | 10/1894 | North | 92/92 |
| 577,887 | 3/1897 | Stanton | 417/234 |
| 1,459,317 | 6/1923 | Birdsall | 92/92 |
| 2,609,000 | 9/1952 | Mowbray | 92/161 |
| 4,187,845 | 2/1980 | Dror | 128/205.13 |

FOREIGN PATENT DOCUMENTS 338229  3/1936  Italy ................. 128/205.17

Primary Examiner—Henry J. Recla

[57] ABSTRACT

A low non-skidding rack holds a breathing bag against the operating room floor in position to be conveniently squeezed rhythmically by the anesthetist using the ball of his foot, thus reinforcing or even taking over the depressed respiration of his patient, while leaving both his hands free for doing venipunctures and performing other functions. The rack includes at one end a rigid tube, removable for sterilization, which couples a breathing hose coming off the gas machine to the mouth of the gas bag, and at the other end an arm with means for gripping and holding the tail of the gas bag.

6 Claims, 4 Drawing Figures

RACK FOR A FOOT-OPERATED ANESTHETIC GAS BAG

The present invention is a rack or framework for holding a standard tailed anesthetic breathing gas bag horizontally on the operating room floor in a position selected to be convenient for the anesthetist to exert rhythmic compression on it with the ball of his foot and so to reinforce or take over lagging respiration of a patient under general anesthesia. The need for assisting breathing of such patients is very common, and is usually supplied by rhythmic hand squeezing of the anesthetic bag as it hangs beneath the soda lime containers of the gas machine. The anesthetist can, instead, remove this same gas bag, fit it in this invented rack on the floor, and interpose a standard corrugated rubber breathing hose or tube between the bag and the port of the gas machine where it is usually attached.

The anesthetist has many duties, some requiring the cooperation of his two hands, such as fastening the head straps to the gas mask and emplacing additional blood transfusion needles in the patient while the operation is in progress; and many of his duties are more conveniently accomplished if he can take his hand away from the bag and shift his bodily position. Manipulation of the breathing bag on the floor by the foot frees his hands and eliminates the periods when the anesthetist has to neglect his duty to breathe for the apneic patient.

This method with rack and bag on the floor can be easily and quickly set up before the induction of the anesthesia, and employed throughout the operation, even for very long cases, and for all types and sizes of patients. It facilitates the making and charting of observations, and relieves much of the anesthetist's stress.

The common presently used way of liberating the hands by introducing a mechanical respirator or ventilator into the breathing circuit is cumbersome; demands so many adjustments at first as to be unsuitable for a series of short cases; and, should it malfunction, poses a hazard as long as the exact nature of the trouble goes undiagnosed.

But squeezing the bag on the floor with a foot, although a simple procedure, presents problems, which led to invention of the bag rack here described. The bag alone is too round, elusive, and unstable as to position. It moves undesirably along the floor, and skips out from beneath the foot. The bag rack is designed to hold the gas bag on the floor precisely in the position selected for most efficient operation by one or the other foot of the anesthetist. The bag and rack combination is easily positioned or moved by manipulation of the connected hose or by nudging it with the toe of the boot. Except for the rack itself, the method relies on the same rubber bag and hoses which are standard equipment, kept in readiness for use with each gas machine. Assembly and disassembly require only seconds of time. The rigid tube or hose-to-bag coupling element of the rack, which is used to join the corrugated breathing tube or hose coming off the gas machine to the pedal gas bag on the floor, comes free with the act of uncoupling, and can be sterilized by hospital employees as easily as the hose and bag; or it may be immersed in 70% alcohol, then stored in the anesthetist's bag.

Compared to squeezing by hand, my method liberates both hands of the anesthetist; and also frees him to move about, for instance in order to perform a venipuncture, since he can reposition the pedal bag over a very wide area of floor space.

The parts are so few and the operation is so simple and natural as to be fail-safe. With this method, patients routinely get better care. Precision of foot operation is comparable to that of the motorist operating the accelerator pedal of a car while shifting gears, or applying the brakes. In fact, the previous driving experience makes the anesthetist already half-trained in the new ventilation technique.

The rack has the general shape of an oval frame and is of very low profile on either side where it comes to lie beneath the foot of the operator but cannot get in the way of the foot as it compresses the bag; and it has no parts intruding centrally where the lower side of the bag gets pressed against the floor.

Separation and compression of gases is expensive of both money and energy; thus whenever pedal bag ventilation could be substituted for ventilation by machine, important savings are possible. This would be especially true for hospitals in developing countries where gases may have to be shipped from long distances in small tanks at considerable cost. Shortages of trained help in these places create delays at times, just when the anesthetist needs prompt help; but pedal ventilation could release his hands to better serve the patient at such and other times.

Routinely, here and abroad, the anesthetist spends many hours daily, seated, squeezing the breathing bag. A secondary benefit of pedal bag ventilation is the exercise of the anesthetist's legs which it provides. This is healthful in a general way, and is especially good for prevention of saphenous phlebothrombosis.

The following description and drawings disclose how my invention works, for improving the technique of anesthesia-giving.

Figure 1:
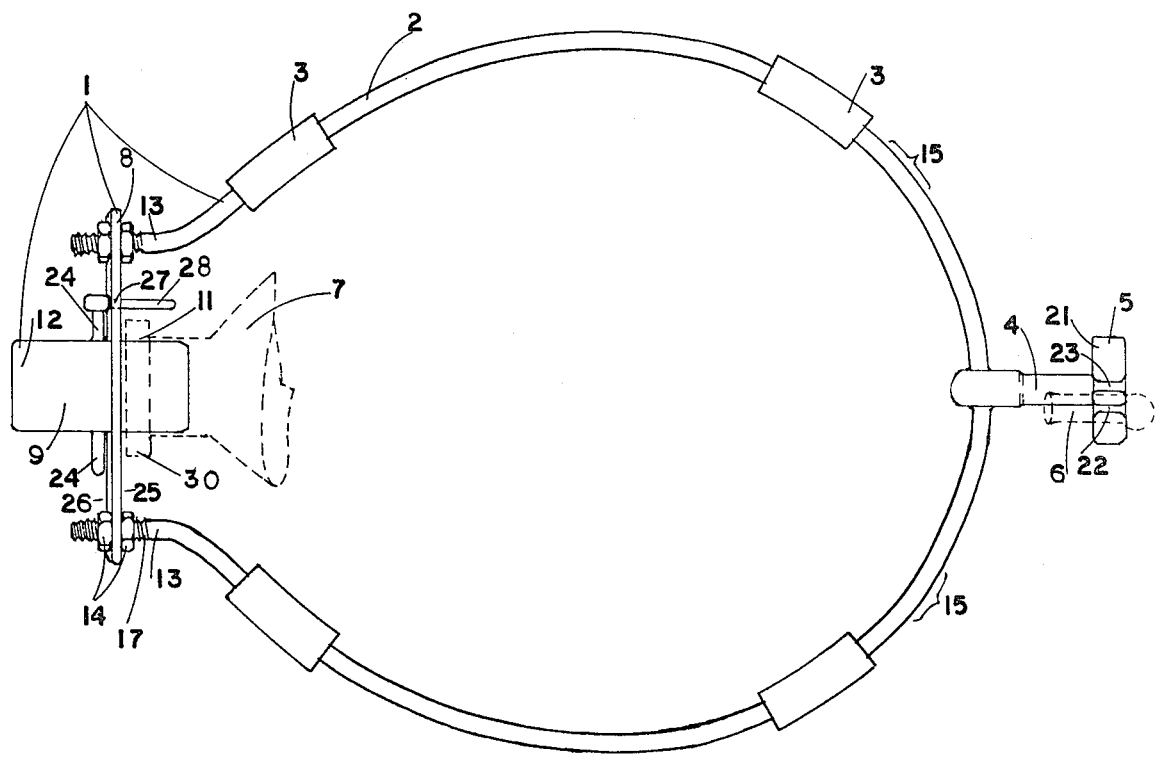
FIG. 1 is a diagram of an embodiment of the invention viewed from above.
Figure 2:
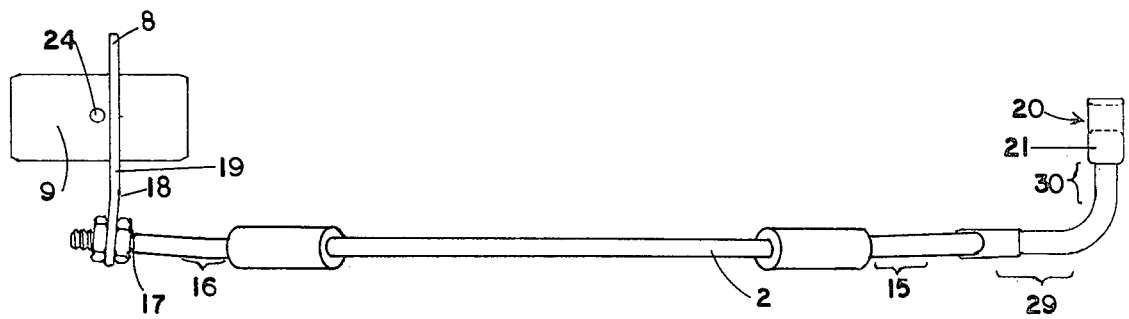
FIG. 2 is a side view.
Figure 3:
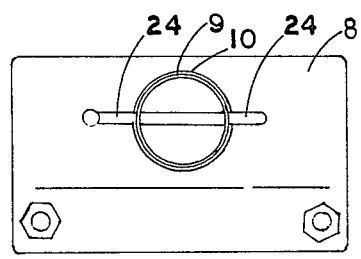
FIG. 3 is a partial view of the bag mouth end of the rack in one embodiment.
Figure 4:
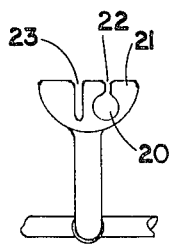
FIG. 4 is an end view detail of the bag tail holder in one embodiment.

The rack or framework 1 for the foot-operated anesthetic gas breathing bag or pedal bag consists of a rigid, curving, roughly U- or horseshoe-shaped main frame part 2 bearing a plurality of four or more electrically conductive rubbery, non-skidding supports spaced well apart 3, resting on the floor while holding the rack off it at a low elevation, a rigid and rigidly attached arm 4 extending upward from the middle of the main frame part, having at its upper end means 5 for holding the tail 6 of a standard anesthetic gas bag 7, an upright plate 8 rigidly attached to the main frame part, completing the frame, and a rigid tube or hose-to-bag coupling 9 inserted in a hole 10 in the upright plate, the rigid tube being of a size to fit tightly by its one end inside the bag's mouth 11 and by its other and outer end 12 to fit tightly inside the end of a standard corrugated breathing tube or hose of a gas machine, a hose of the type that ordinarily leads from the gas machine to the Y-piece for the face mask. The corrugated tube's other, distal end is fitted on the port of the gas machine which ordinarily holds the gas bag.

In one embodiment of the invention, the curving main frame part consists mostly of 3/16 inch round rod formed into an oval having the two ends 13 parallel to one another and threaded far back enough so that the upright plate can be secured near the ends by nuts 14 tightened one to either side of each of two holes in the plate made for accommodating the threaded rod ends. In this particular embodiment, gripping to provide immobilization with reference to the floor is obtained by four lengths each approximately an inch long of tightly-fitting thick conductive rubber tubing 3 spaced far apart along the rod after being slip-threaded on it, before the nuts and upright plate are attached. The main frame part need not be made of rod at all, and the rubber feet may be of conventional type. The main frame part has a slight curve 15 away from the floor near its middle, raising its junction with the bag tail-holding arm, also a similar curve 16 close to where the threads end 17, so that all metal parts which could otherwise slide on the floor are lifted slightly off by the non-skidding rubbery supports or feet.

The upright plate has a horizontally disposed angulation 18 running above its lower edge and the holes for the threaded rod ends; and thus the part 19 of the plate above this angulation and which bears the hose-to-bag coupling is held vertically.

The bag tail-holding arm in one embodiment has a horizontal hole 20 in its expanded distal end 21, parallel with the long axis of said rack and about 1½ inches above the floor, of a bore a little smaller than the outer diameter of the bag's hollow tail, so that the part grips the tail tightly after the tail is inserted in the hole. A slot 22 running the length of the hole allows for easy insertion of the tail upon stretching and flattening distortion. A second and deeper slot 23 close beside the first but not widened and rounded out in depth is provided so that the tail extending beyond the hole can be doubled back and inserted in the second slot, then drawn taut, thus sealing it shut in the event that the normally closed end has been snipped off and thus opened. Certain marketed gas bags have very short tails. These tails are gripped and held securely in the deep straight-walled slot, in which case the slot leading to the rounded-out hole need not be used. The edges of the arm are well rounded off, facilitating insertion and removal of the tail without damage to it.

In one embodiment, the long axis of the main frame part is moderately shortened, and the bag tail-holding arm extends to its required position under the tail by first extending horizontally 29 away from the main frame part 2, then extending vertically upward 30. In another embodiment, this arm ascends slanted upward and outward to reach the required position.

Hose-to-bag coupling 9 has projections 24 near its middle to assist the grip in the twisting on or off of the tightly-fitting hose and bag as the coupling lies in its hole in the upright plate and as the bag mouth and hose end are brought close to each other from the inner 25 and outer sides 26, respectively of the plate. Hole 10 for the coupling is median in the plate and is centered roughly 1½ inches above the floor. The plate has an additional smaller hole 27 for receiving a slender extension 28 of one of the projections 24, running parallel to the long axis of the coupling. When this extension is in this hole, rotation of the coupling in its hole is prevented, thereby preventing twisting and winding up of the bag, with loss of capacity. This extension and its hole are spaced far enough away from any bushing, ferrule, or other thickened ring 30 forming the bag's mouth that the extension will not impinge, and interfere with insertion of the coupling in the bag mouth. With assembly completed, projections 24 and the sited bag's mouth cooperate in retaining coupling 9 in position in upright plate 8.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range are intended to be embraced herein.

Desiring to secure Letters of Patent of the United States, and having described my invention, I herewith set forth my claims.

1. I claim a rack for holding a manufactured tailed preferably electrically conductive anesthetic gas breathing bag against the floor of an operating room, in selected fixed positions by its tail and by a rigid hose-to-bag coupling fitting tightly in said bag's mouth and also tightly in one end of a manufactured corrugated rubbery breathing tube which is connected properly by its other end to a gas machine, and of the kind commonly used in the anesthetic breathing circuit between the gas machine and the face mask's Y-piece, said rack so structured that it leaves a large area of the floor unoccupied centrally for broad contact with the bulging belly of said bag while holding the mouth and tail of said bag a little elevated off said floor and while maintaining a low profile on both sides of said bag, thus making room for the anesthetist's ball of the foot to rhythmically and without obstruction compress said gas bag and ventilate the patient's lungs; said rack comprised of a frame and the said hose-to-bag coupling, and said frame being a combination of an oblong main frame part of low elevation adapted to be beneath the sides of said bag and spaced low off the floor by a plurality of low rubbery electrically-conductive non-skid cushions underneath, a rigid bag tail-holding arm rigidly attached to one end of said main frame part and extending upward where, near its terminus, it has a means for securing said bag's tail, and also an upright plate opposite and across from said bag tail-holding arm and rigidly fastened to said main frame part and having a hole therein said hose-to-bag coupling comprising a length of tubing slidably fitted without tightness in said hole and having projections extending laterally from the middle thereof, said coupling being held in said hole, during the ventilations, by the bag mouth on one side of said plate and some projections from near the middle of said coupling on the other side.

2. I claim the device of claim one wherein, in one embodiment, said main frame part is of roughly a U or horseshoe shape and consists mostly of a rod of roughly 3/16 inch diameter, having both ends parallel to one another and threaded back far enough to each accept at least two common nuts of matching threads as well as said plate where it has holes into which said rods fit, wherein said plate, at each of these two bolt holes in it, is secured on said threaded rod ends by two nuts tightened toward each other, one on either side of each bolt hole, wherein said main frame part near its middle and junction with said bag tail-holding arm curves slightly away from said floor, wherein the rod material curves slightly away from the floor also starting just back from its two threaded ends, said curves keeping downward projections of said frame off said floor where they might cause skidding, wherein said rod material bears a plurality of at least four lengths of thick anti-skid rubbery tubing, fitting tightly on, separated far apart, and of a thickness to space all rigid parts of the underside of said rack slightly off said floor, thus preventing sliding, and wherein, for reducing the length of said main frame part, the bag tail-holding arm does not just rise vertically up under the bag's tail but rather extends outward and away from its attachment to a shortened main frame part as well as extending upward.

3. I claim the device of claim one wherein said bag tail-holding arm is thick distally and has near its upper end a horizontal hole paralleling the long axis of the rack and roughly 1½ inches above the floor and of a size a little smaller than the outer diameter of said bag's tail, said hole being slotted open along its length, and these features being so proportioned that the tail when stretched and flattened may be inserted at the slot, to round up and be gripped and to fit tightly in said hole, wherein a second and deeper slot is made beside the first, but is not widened and rounded out in depth, providing for a second insertion of said tail farther along its length thereby doubling back said tail, which, especially if cinched up, becomes tightly closed off in the event that the normally closed end has been previously snipped off with conversion of said tail into an open hose, wherein said second slot furthermore provides a separate means of anchoring the tail for the manufactured short-tailed variants of breathing bags upon stretching and insertion of the tail, and wherein fixations and removals of said tails are facilitated, and without damage, by adequate rounding off of the edges of said arm.

4. I claim an embodiment of claim one wherein, to conserve material and overall size, said frame is moderately shortened so as not to extend all the way to directly beneath the tail of said bag and wherein said bag tail-holding arm extends both radially away and upward from its attachment to said frame.

5. I claim the device of claim one wherein an upright plate is fixed rigidly on the said main frame part and has a median hole centered roughly 1½ inches above the floor, about as high as the horizontal hole of said bag tail-holding arm, and of a size that through it said hose-to-bag coupling is passed without tightness to about half-way, wherein said upright plate has also a neighboring smaller hole for receiving an elongated extension of one of two or more grip-aiding projections from near the middle of said coupling, the said elongated extension fitting in the said neighboring smaller hole and thus preventing rotation of said coupling and winding up of said bag, and wherein said upright plate has a slight horizontally disposed angulation above its lower edge and above the holes for the threaded rod ends, so that the plate part above the angulation is held vertically.

6. I claim the device of claim one wherein said hose-to-bag coupling fits without tightness in the median hole of said upright plate and fits tightly by its projecting end into one end of said corrugated rubbery breathing tube and fits tightly by its inner end into the mouth of said gas bag, wherein said coupling has two or more projections outward from about its middle to aid the grip when the rubbery parts are being twist-fitted on it, wherein the end of one of said projections leads to a slender extension integral with said projection and paralleling said coupling's main axis, said extension of a length to be held in said smaller hole in said plate and spaced away appropriately from said coupling's tube so as to enter said smaller hole when said coupling is emplaced, wherein said slender extension and its hole are spaced far enough away from any bushing, ferrule, or other thickened ring forming said bag's mouth that the said extension will not impinge, and interfere with insertion of the coupling in the bag's mouth, and wherein said projections from said coupling, in cooperation with said emplaced bag's mouth, combine to secure said coupling in working position near its middle in said median hole of said upright plate.

* * * * *